US006632662B1

(12) United States Patent
Broyer et al.

(10) Patent No.: US 6,632,662 B1
(45) Date of Patent: *Oct. 14, 2003

(54) DEVICE AND METHOD FOR THE LYSIS OF MICRO-ORGANISMS

(75) Inventors: Patrick Broyer, Villeurbanne (FR); Philippe Cleuziat, Lyons (FR); Bruno Colin, Marcy l'Etoile (FR); Cécile Paris, Marcy l'Etoile (FR); Lyse Santoro, Charbonnieres les Bains (FR)

(73) Assignee: Bio Merieux, Marcy l'Etoile (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/743,723
(22) PCT Filed: Jun. 3, 1999
(86) PCT No.: PCT/FR99/01309
§ 371 (c)(1),
(2), (4) Date: Mar. 2, 2001
(87) PCT Pub. No.: WO00/05338
PCT Pub. Date: Feb. 3, 2000

(30) Foreign Application Priority Data

Jul. 23, 1998 (FR) .............................................. 98 09583

(51) Int. Cl.[7] .......................... C12M 1/33; C12M 1/00; C12M 1/06
(52) U.S. Cl. .................. 435/306.1; 435/259; 435/283.1
(58) Field of Search .............................. 435/259, 283.1, 435/306.1

(56) References Cited

U.S. PATENT DOCUMENTS 5,643,767 A 7/1997 Fischetti et al.

FOREIGN PATENT DOCUMENTS

FR 2 768 743 3/1999

OTHER PUBLICATIONS

Melendres et al., A kinetic analysis of cell disruption by bead mill, 1991, Bioseparation, vol. 2, pp. 231–236.*

* cited by examiner

Primary Examiner—James Ketter
Assistant Examiner—Daniel M. Sullivan
(74) Attorney, Agent, or Firm—Oliff & Berridge, PLC

(57) ABSTRACT

The invention concerns a device for lysis (1) of microorganism to release at least one intracellular biological constituent, comprising a container (2) wherein are present a biological sample, in liquid medium, containing the microorganism to be lyzed, and a material in the form of particles, relatively hard and inert with respect to the sample. The invention also concerns a grinding method. The material in the form of particles comprises at least two types of grinding means into different dimensions: at least large dimension magnetic means (3) automatically controlled by a magnetic field; and at least small dimension means (4) actuated by the large dimension grinding means (3). The invention is useful for separating biological constituents.

23 Claims, 2 Drawing Sheets

DETAIL B

SECTION A-A

DETAIL B

DEVICE AND METHOD FOR THE LYSIS OF MICRO-ORGANISMS

The present invention relates to a novel device for the lysis of micro-organisms making it possible, by completely or partially destroying the membrane, to release at least one intracellular biological component. It also relates to a lysis method employing a device as defined hereinabove.

The state of the art describes a method which is generally used for cell lysis, and which essentially consists in placing, in a container, a biological sample in liquid medium, comprising the micro-organism to be lysed. Next, at least one material in the form of particles, relatively hard and substantially inert with respect to the biological components is added to the container and finally the mixture consisting of the biological sample and of the material in the form of particles is subjected to a vortex-type motion.

This method used exhibits certain disadvantages. Thus, it has been noticed that the lysis method commonly used is not sufficiently efficient, and that, in particular, the cell lysis proves insufficient in terms of quantity and in terms of quality.

In addition, the method employed does not always allow the lysis of cells which are deemed to be lysis-resistant, like Gram-positive cells such as mycobacteria, for example.

Likewise, implementation of the method often entails adding additional reagents, particularly enzymes and/or detergents.

The applicant company has filed a patent application FR97/12164 dated Sep. 23, 1997, regarding a method for the lysis of micro-organisms.

This lysis method is intended to release at least one biological compound contained in the micro-organism, comprising a lysis step wherein:

a biological sample in a liquid medium, comprising the micro-organism that is to be lysed, is placed in a container, at least one material in the form of particles, relatively hard and substantially inert with respect to the biological compounds, is placed in said container, and the mixture of the biological sample and of the material in the form of particles is subjected to a vortex-type motion.

The method uses a material in the form of particles which comprises beads with a diameter of between 90 and 150 µm, and which satisfies the following equation:

$$Ve = \beta Vb,$$

where Vb is the apparent volume of the beads, Ve is the volume of the liquid sample and a is a number between 1.4 and 10 when the container is of tubular shape, and less than or equal to 2.1 when said container is of diskoid shape.

These characteristics are still particularly advantageous and the content of that patent application is to be considered as being contained in the description of the present invention.

Document U.S. Pat. No. 5,643,767 proposes a container to allow cellular components such as ribonucleic acids (RNAs) to be isolated from cells present in a liquid solution. To do that, this container contains two types of bead, which differ in terms of their diameter. The first type, of small size, is made of glass or metal with a diameter of between 0.1 and 1 millimeter. The second type, of large size, is made of the same material, glass or metal, with a diameter of between 3 and 5 millimeters.

The essential disadvantage with this device lies in the fact that whether the vortex is mechanical or magnetic, the motion of the beads is homogeneous.

However, the applicant company, through sustained effort and additional work, kept up these studies into the field of vortex-type-motion magnetic lysis and succeeded in determining characteristics allowing vortex-type agitation in a container without the container needing to be mechanically agitated, as is the case with a mechanical vortex. Thus, by adding beads of essentially two different diameters, it is possible to considerably increase the efficiency of said lysis, improving the release of the intracellular components. It is also possible, for the same efficiency of lysis, to reduce the time taken to achieve this lysis, which is something which may prove particularly beneficial in the case of diagnostic tests which have to be performed quickly.

To this end, the present invention relates to a device for the lysis of at least one species of micro-organism, so as to release at least one intracellular biological component, which comprises a container in which there are, on the one hand, a biological sample in liquid medium, which contains the micro-organism to be lysed and, on the other hand, at least one material in the form of particles, which is relatively hard and substantially inert with respect to the biological compounds of the sample, characterized in that the material in the form of particles comprises at least two types of grinding means of different sizes:

at least one large-sized magnetic means which is slaved to the movement of a magnetic field, and at least one small-sized means which is set in motion by the large-sized grinding means.

The material in the form of particles comprises, by way of large-sized grinding means, at least one large-diameter bead and, by way of small-sized grinding means, at least one small-diameter bead.

The ratio between the sizes of the small-sized grinding means and the size of the large-sized grinding means is between 1/10 and 1/100, preferably between 1/30 and 1/60 and, more specifically, this ratio is 1/40.

In addition, the ratio between the size of the micro-organism to be lysed and the size of the small-sized grinding means is between 1/10 and 1/100, preferably between 1/30 and 1/60, and more specifically is 1/50.

Another characteristic: the ratio between the total volume of the small-sized grinding means and the volume of the biological sample containing the micro-organism to be lysed is between 1/2 and 1/5 and is preferably 1/3.

The number of large-sized grinding means is between 1 and 10 and preferably between 1 and 4.

In a first preferred embodiment, the container is of tubular shape.

In a second preferred embodiment, the container is of diskoid shape.

Whatever the embodiment used, each large-sized magnetic grinding means is moved by the rotary motion about the tube of at least one permanent magnet.

In addition, each large-sized magnetic grinding means is moved by the rotary motion under the tube of at least one permanent magnet.

When the container is of diskoid shape, each large-sized magnetic grinding means collaborates with a roughly circular runway located at the periphery of the container.

The present invention also relates to a method for the lysis of at least one species of micro-organism in a biological sample so as to release at least one intracellular biological component, which uses, in a container, at least one material in the form of particles, forming a grinding means which is relatively hard and substantially inert with respect to the biological compounds in the sample, characterized in that it consists in:

placing at least one large-sized magnetic grinding means, at least one small-sized non-magnetic grinding means and a biological sample containing the micro-organism that is to be lysed in the container, placing the magnetic grinding means in a moving magnetic field so as to generate a vortex motion in the mixture, and stopping the effect of the magnetic field on said magnetic grinding means.

In a first mode of operation, the magnetic field can rotate about the container at the height of the biological sample.

In a second mode of operation, the magnetic field can rotate under the container at the height of the biological sample.

Whatever the mode of operation, the rotary magnetic field applies to the magnetic grinding means located in the biological sample a field which is alternately strong and weak.

The FIGS. appended hereto are given by way of explanatory example and are entirely non-limiting. They allow better understanding of the invention.

Figure 1:
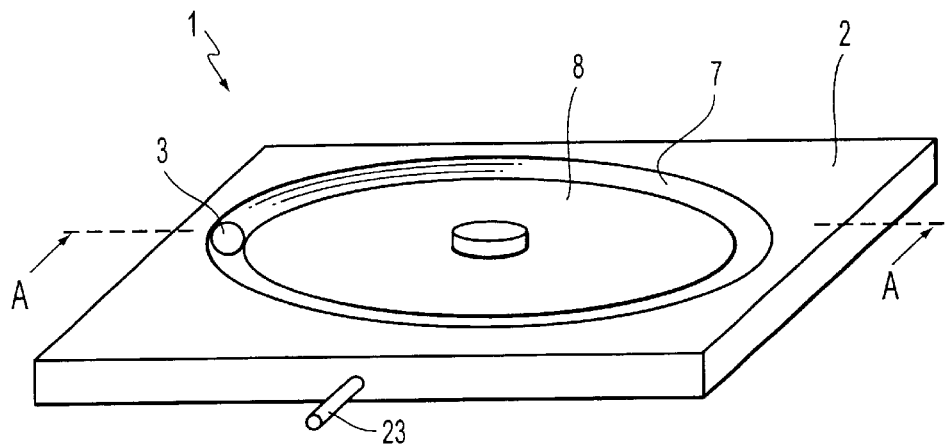
FIG. 1 is a perspective view of a lysis device according to the invention, in an embodiment of diskoid shape.
Figure 2:
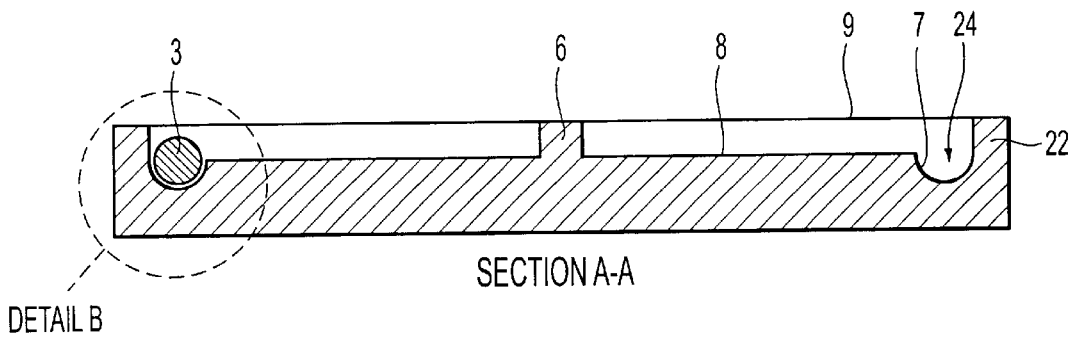
FIG. 2 is a view in section on A—A of the device shown in FIG. 1.
Figure 3:
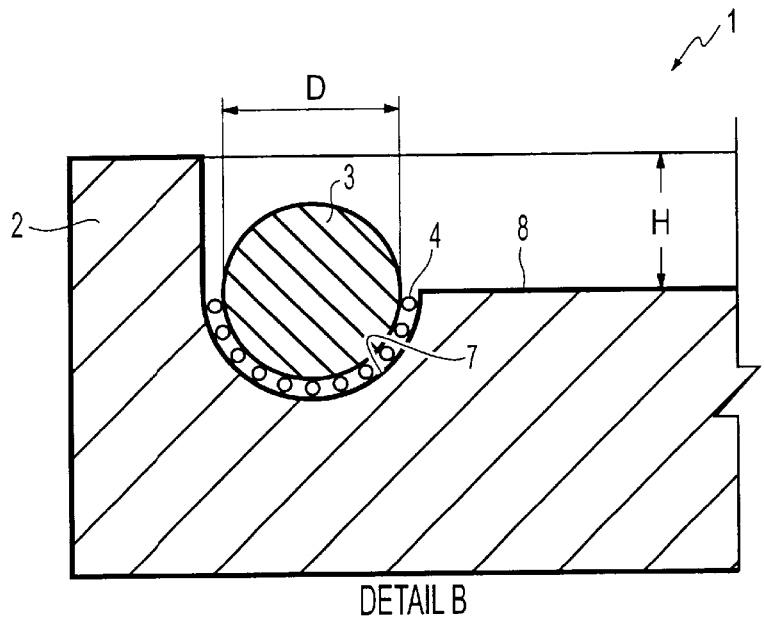
FIG. 3 depicts a large-scale view of detail B shown in FIG. 2.
Figure 6:
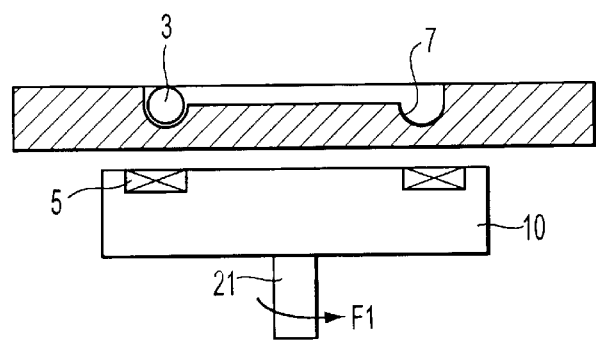

Finally, FIG. 6 is a schematic side view of the lysis device of diskoid shape, shown in FIGS. 1 to 3, in which said device is associated with a third type of magnetic apparatus, allowing the lysis device to operate correctly.

The present invention relates to several lysis devices clearly depicted in the collection of FIGS. 1 to 6.

The first lysis device 1 is depicted in FIGS. 1 to 3 and 6. It essentially consists of a container 2, also known as a card, of essentially parallelepipedal shape comprising, on its upper surface, a recess in which lysis is performed.

This recess essentially consists of a runway 7. This runway 7 is located at the periphery of the recess. At the center of said recess there is a stud 6, of which the upper surface, in the position which is that of FIGS. 1 to 3, is at the same level as the upper surface of the lateral edges 22. Located between the central stud 6 and the runway 7, there is an intermediate area 8. The recess formed by the stud 6, the runway 7 and the intermediate area 8 is bounded by a partitioning means also known as a partitioning film 9.

As can be clearly seen in FIG. 3, the runway 7 collaborates with two grinding means 3 and 4. The first grinding means 3 is a large-diameter grinding means, whereas the grinding means 4 is a small-diameter grinding means. In fact, the grinding means 3 consists of a magnetic bead 3, while the grinding means 4 consists of a number of small-diameter beads 4.

Still according to FIG. 3, it is obvious that there is a ratio between the diameter D of the bead 3 and the height H between the intermediate area 8 and the partitioning means 9. Thus, to prevent the large-diameter bead 3 from leaving the runway 7, the diameter D is greater than the height H.

There is also a ratio between the sizes of the bead 3 and of each bead 4. Thus, the bead 3 is magnetic and has a diameter of roughly 2 millimeters (mm), whereas the beads 4 are made of glass and have a diameter of fifty micrometers ($\mu$m). There is therefore a ratio between each bead 4 and the bead 3, which is one in forty.

Likewise, there is a ratio between the small-diameter glass beads 3 and the bacteria, which, as a general rule, are about one micron in size, the ratio between bacterium and bead 4 is therefore one in fifty.

It is entirely possible to use other sizes and therefore other ratios. For example, 200 $\mu$m beads have been successfully used, the ratio then being one in two hundred.

Of course, the width of the runway 7 has to be slightly greater than the diameter D of the large-diameter bead 3. In this particular instance, the width of the runway 7 is 2.2 mm.

Likewise, it is important for there to be a ratio between the total volume of the small-sized grinding means 4 and the volume of the biological sample containing the micro-organism to be lysed. As a general rule, this ratio is between one in two and one in five but is preferably one in three.

In the embodiment depicted in FIGS. 1 to 3, there is just one large-diameter bead 3 whereas there are a great many small-diameter beads 4. The only essential feature is, of course, to respect the ratio that has to be between the volume of the beads 4 and the volume of the biological sample. Of course, the biological sample has not been depicted in these figures.

According to FIG. 1, a means 23 for introducing the biological sample into the space delimited by the partitioning film 9 and the recess is depicted. This means of introduction 23 opens out inside the recess at the runway 7.

Motion inside the container 2 is generated, as depicted in FIG. 6, by magnets 5 located at a support 10. This support 10 is mounted on a rotation spindle 21. This rotation spindle 21 is associated with a motor, not depicted in this figure but referenced 20 in FIG. 5, which drives the spindle 21 with a motion along F1. The rotational motion F1 gives rise to movement of the magnets 5, of which there may be two as depicted in FIG. 6, but of which the number is non-limiting; there may be one or three, four or more of them. In any case, the magnet 5 will cause the large-diameter bead 3 which is made of magnetic material to rotate on itself and also along the runway 7. The motion of the bead 3 will also give rise to motion of the small-diameter beads 4 which are made of glass and which are therefore moved only via this bead 3 and via the liquid flow generated by the motion of said bead 3. The smaller diameters of the beads 4 will increase the surface areas of contact between the beads 4 and the wall of the runway 7, on the one hand, and between said small-diameter beads 4 and the large-diameter bead 3, on the other hand, thus making it possible to significantly increase the number of impacts and interactions (the amount of shear) between the glass beads and the bacteria or yeasts, which destroy the membranes of the micro-organisms and thus enhance the release of the intracellular biological components, which is improved.

Nonetheless, it is entirely possible to use the container 2 in a position other than the one depicted in FIG. 6. Thus, it is possible to position the orifice of the means of introduction 23, which opens out into the runway 7, in such a way as to avoid the small beads 4 dropping into said means 23 simply under gravity.

Figure 4:
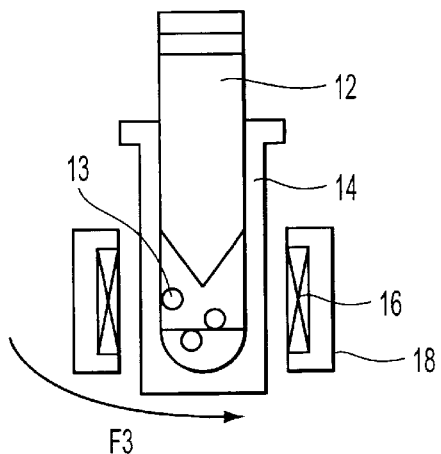
FIG. 4 is a schematic side view of a lysis device according to the present invention, in an embodiment of tubular shape, but with which a first type of magnetic apparatus is associated, allowing the device to operate correctly.

According to a second embodiment, depicted in FIG. 4, the lysis device 11 uses a tube 12 by way of container.

This container 12, like the previous one referenced 2, is made of polystyrene or polypropylene.

Figure 5:
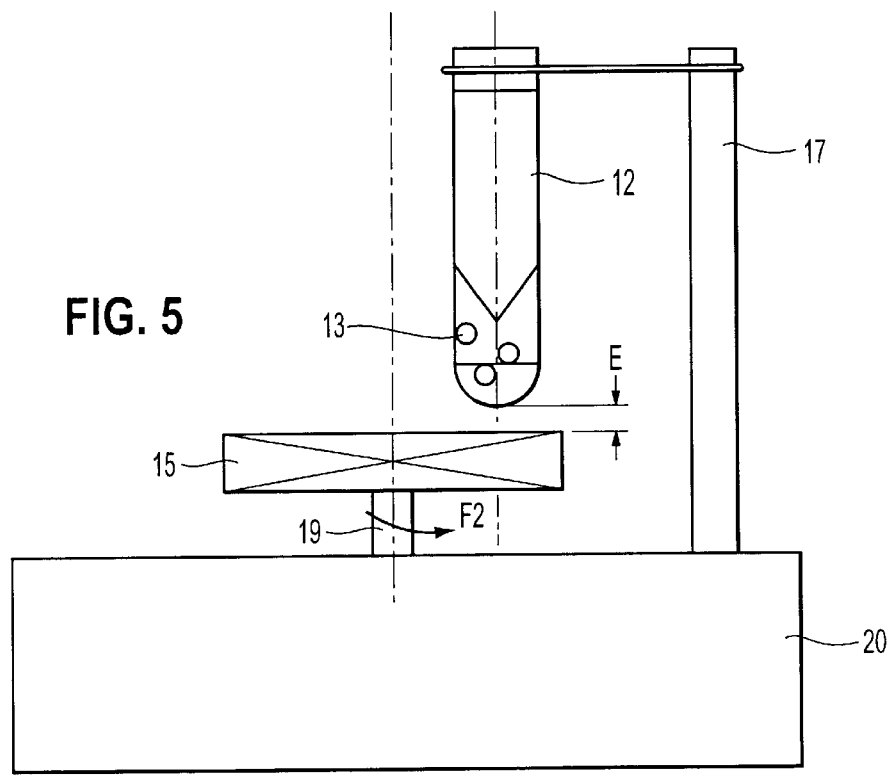
FIG. 5 is a view roughly identical to the one shown in FIG. 4, in which the device is associated with a second type of magnetic apparatus, allowing the device to operate correctly.

Two sets of apparatus are described in FIG. 4 and FIG. 5 that allow the use of such a tube 12.

According to FIG. 4, lysis is performed in the tube 12 via large-sized grinding means 13 which are of course associated with small-sized grinding means in the same ratio established for the first embodiment depicted in FIGS. 1 to 3, but which have not been depicted in this FIG. 4. Nonetheless, it will be fairly easy to understand that the operation will be identical except that in this instance the runway is replaced by the lateral edges of the tube 12. This tube 12 is located in a support 14 which allows the tube 12 to be positioned correctly with respect to means. These means allow the large-diameter magnetic beads 13 located in the container 12 to be subjected to a magnetic field. In this case, note the presence of permanent magnets 16, located around the container 12 and themselves secured to one another by a ring-shaped support 18 depicted partially in this FIG. 4. the support 18 and magnets 16 assembly is given a rotational motion about the tube 12 and its support 14 along F3, and thus causes the large-diameter beads 13 to move. In this particular instance there are three of these beads 13. Tests have also been carried out with five, ten or fifteen beads.

According to FIG. 5, the container 12 also comprises large-diameter beads 13, three of them. In this instance the support consists of a bracket 17 which holds the upper part of the tube 12. In fact, in this instance, the magnet 15 is positioned lower down than the tube 12, so that the rotational motion generated at the motor 20 along F2, is transmitted to the magnet 15 via the spindle 19, which will cause motion in the beads 13. According to this figure, the beads 13 are subjected alternately to a field gradient which is strong and then weak, as the permanent magnet moves away from or closer to the tube 12, this driving said beads 13 with a motion that creates shear forces due to the small-diameter beads, which again have not been depicted in this figure. It should be noted that for this configuration to have optimum effect, the distance E between the bottom of the tube 12 and the magnet 15 needs to be as small as possible. A separation E of 0.5 to 4 mm can be used, and this separation is preferably 1 mm. It will be noticed in FIGS. 4 and 5 that the biological sample present in the tube 12 is given a vortex motion so that a kind of cone shape is created at the free upper part of the liquid. As far as FIG. 6 is concerned, it will be noticed in this figure that there is no stud 6 at the central part of the container 2. In fact, this stud is absolutely non-essential, because it has no role to play in the system's lysis function. By contrast, it has a role of supporting the transparent polypropylene film 9 which delimits the lysis space.

The examples which will follow show the way in which the various embodiments of the lysis device work and show its effectiveness by comparison with the conventional mechanical lysis system.

The embodiment of FIGS. 1 to 3 and 6 will, hereinafter, be referred to as the diskoid card, the embodiment of FIG. 4 will, for its part, be referred to as a lateral vortex, and the embodiment of FIG. 5 will, itself, be referred to as a longitudinal vortex.

EXAMPLES

1—Card Format (Diskoid) Magnetic Vortex

This embodiment essentially corresponds to FIGS. 1 to 3 and 6.

A—Procedure:

The lysis protocol was performed in the card-format container 2, on two types of micro-organism cultured the day before: *Staphylococcus epidermidis* bacteria, on the one hand, and *Candida krusei* yeast, on the other hand.

The card 2 used has the following characteristics. The sides were 4 centimeters (cm) long and it was 0.4 cm tall. It was equipped with a closed-ended well about 0.37 cm tall from the bottom of the runway or furrow 7 to the edge of the upper face and with an outside diameter of 3 cm. The diameter of the furrow 7 in which the iron bead 3 moves was 0.22 cm. The iron bead or beads 3 had a smaller diameter of about 0.19 cm so that they could be highly mobile. In the tests described, just one iron bead 3 was used.

The well was closed with a transparent self-adhesive film 9 and filled with glass beads 4 100 micrometers ($\mu$m) in diameter for the lysis of the *S. epidermidis* bacteria and 400 to 600 $\mu$m in diameter for the lysis of the *C. krusei* yeasts. The iron bead 3 used for agitating the glass beads 4 was positioned in the furrow 7 of the card 2 beforehand. Said card 2 was filled with the suspension of micro-organisms to be lysed and finally positioned horizontally on the rotary magnets 5 system.

The lysis protocol was performed for a duration of 5 minutes (min) at maximum speed, namely approximately 2800 revolutions per minute (rpm). In each case, an iron bead 3 and 600 $\mu$l of sample volume (*S. epidermidis* or *C. Krusei*) were used. The apparent volume of the glass beads 4 varied from 30 to 180 $\mu$l. Cards 2 with and without the central stud or pip 6 (allowing for easier positioning of the self-adhesive film 9) were used indiscriminately.

B—Results:

The OD measurement was not reliable enough to evaluate the lysis percentage. The cleanliness of the lysis beads 4 (100 and 500 $\mu$m) was of poor quality, and significant release of particles from said beads 4 seemed to occur during lysis. This release significantly altered the OD measurement and therefore biased the result of the bacterial lysis. Initially, the OD measurements were not therefore used, but were not, however, needed to demonstrate the effectiveness of the magnetic vortex methods described.

Following the magnetic vortex step, the lysate was recovered and then analyzed on 0.8% agarose gel. the gel allowed an evaluation of the amount of nucleic acids released by the lysis (the intensity of the band) and their state of preservation (whether the band was very narrow and sharply defined or whether it was a very long smear). A photograph of the gel showed, in its upper part, the migration of the nucleic acids of *S. epidermidis* bacteria released and, in its lower part, the migration of the yeast nucleic acids released.

In each case, a migration control on a non-lysed initial suspension was loaded into the first well. The gel was checked, in both instances, to ensure that no nucleic acid band appeared before the lysis. The lysis results were also compared with the result of the reference method, that is to say lysis by mechanical vortex according to the experimental conditions described in the procedure.

In the case of the lysates of the *S. epidermidis* bacteria, it was found that although the intensity of the bands was weak compared with the mechanical vortex control, the DNA bands and the two RNA bands were visible and of an intensity that varied according to the experimental conditions.

Some of the tests, referenced 2, 4, 5, 6, 7 and 8, were obtained with 30 $\mu$l of VIAI beads 4, with a diameter of 100 $\mu$m, in 600 $\mu$l of bacterial suspension. It was found that the bands were visible but of very weak intensity, which means that very few nucleic acids were released.

One test, referenced 1, was performed with 180 $\mu$l. The nucleic acid band was also not very visible. This is explained by the excessively high amount of beads 4 with respect to the dimension of the furrow 7 in which the iron bead 3 revolves. As the rotational speed of the bead 3 was low, the agitation of the beads 4 was not very effective and the release of nucleic acids was therefore not very great.

Another test, referenced 3, was performed with 90 $\mu$l of beads 4 in 600 $\mu$l of suspension. It was clearly seen on the gel that the intensity of the bands was markedly greater than in the previous tests. The gel also showed that the nucleic acids were in the same state of preservation as those released with the mechanical vortex.

In conclusion, the effectiveness of the lysis is very much dependent on the ratio of beads 3 and 4 with respect to the sample volume and also depends on the ratio between the sample volume and the total volume of the diskoid well 24.

In these tests, the optimized amount of beads 3 and 4 is probably, in the case of the diskoid container 2 tested, somewhere between 90 and 180 $\mu$l. The choice of correct ratios between amount of beads, amount of sample and well volume makes it possible to significantly improve the efficiency of the lysis and obtain performance identical to that of the mechanical vortex, but without its drawbacks such as noise and vibration.

In the case of the lysates of the *C. krusei* yeasts, as for the bacterial suspensions, it was found that the intensity of the nucleic acid bands, that is to say the amount of material released, depended on the experimental conditions.

The tests referenced 6 and 7 were performed with 30 $\mu$l of beads 4 500 $\mu$m in diameter in 600 $\mu$l of yeasts suspension. It was found that the bands were visible, but of very low intensity, which meant that very few nucleic acids were released. The amount of beads 4 was therefore too low with respect to the volume of sample to be lysed.

The tests referenced 1 and 2 were performed with 60 $\mu$l of beads 4, still in 600 $\mu$l of suspension. The nucleic acid bands were a little more visible, but were still not very intense compared with the mechanical vortex controls. During these tests, significant blockages were noted when the iron bead 3 was being rotated, as was a significant amount of stagnation of part of the suspension for lysis at the central pip 6. This explains the difference compared with the tests referenced 3 and 4 for which the DNA/RNA bands are clearly visible and more intense than for the other tests.

It will be noted that, like for the bacterial suspensions, the nucleic acids were perfectly preserved.

The same conclusions are valid here as were valid for the tests on bacteria. The amount of glass beads 4 needs to be optimized with respect to the sample volume and the volume of the well 24. The rotational speed of the bead 3 and the duration of the vortex are two factors which are also very important in directly influencing the amount of nucleic acids released.

2—Tubular Format (Lateral) Magnetic Vortex

This embodiment essentially corresponds to FIG. 4.

A—Procedure:

The lysis protocol was carried out in the tube-format container 12 of the Falcon type with a U-shaped bottom (diameter×height=12×75 mm) on *S. epidermidis* bacteria cultured the day before.

The tubes 12 were filled with a volume of 600 $\mu$l of bacterial suspension and an apparent volume of 180 $\mu$l of VIAI beads 4 with a diameter of 100 $\mu$m. Various settings were tested with regard to the number of iron beads 3 agitating the suspension, to the number of glass beads 4 of a diameter of 3 mm, to the duration of the vortex and to the rotational speed.

The experimental conditions tested are summarized in table 1 below, where the OD of the initial suspension was 0.672. In this respect, the lysis percentage was calculated by subtracting the parasitic OD value from the measured value. These values are, however, merely indicative and are not to be taken as a criterion for determining the optimum setting of the parameters investigated.

TABLE 1

Study into the effectiveness of a magnetic vortex in tubular format subjected to lateral magnetization

| N° | OD | % lysis | Iron beads | Glass beads | Duration (min) | Voltage (V) |
|---|---|---|---|---|---|---|
| 1 | 0.176 | 0 | 10 | 6 | 2 | Sterile BCC mechanical vortex |
| 2 | 0.338 | 75.9 | 10 | 6 | 2 | *S. epidermidis* mechanical vortex |
| 3 | 0.171 | 0 | 10 | 6 | 5 | 6.5 |
| 4 | 0.558 | 42.4 | 5 | 0 | 5 | 5 |
| 5 | 0.577 | 39.6 | 5 | 0 | 5 | 5.5 |
| 6 | 0.613 | 34.2 | 5 | 0 | 5 | 6 |
| 7 | 0.627 | 32.1 | 5 | 0 | 5 | 6.5 |
| 8 | 0.698 | 21.6 | 10 | 0 | 5 | 5 |
| 9 | 0.542 | 44.8 | 10 | 0 | 5 | 5.5 |
| 10 | 0.614 | 34.1 | 10 | 0 | 5 | 6 |
| 11 | 0.639 | 30.3 | 10 | 0 | 5 | 6.5 |
| 12 | 0.562 | 41.8 | 15 | 0 | 5 | 5 |
| 13 | 0.662 | 26.9 | 15 | 0 | 5 | 5.5 |
| 14 | 0.646 | 29.3 | 15 | 0 | 5 | 6 |
| 15 | 0.643 | 29.8 | 15 | 0 | 5 | 6.5 |
| 16 | 0.696 | 21.9 | 5 | 3 | 5 | 5 |
| 17 | 0.598 | 36.5 | 5 | 3 | 5 | 5.5 |
| 18 | 0.661 | 27.1 | 5 | 3 | 5 | 6 |
| 19 | 0.63 | 31.7 | 5 | 3 | 5 | 6.5 |
| 20 | 0.632 | 31.4 | 10 | 3 | 5 | 5 |
| 21 | 0.608 | 35 | 10 | 3 | 5 | 5.5 |
| 22 | 0.652 | 28.4 | 10 | 3 | 5 | 6 |
| 23 | 0.655 | 28 | 10 | 3 | 5 | 6.5 |
| 24 | 0.672 | 25.4 | 15 | 3 | 5 | 5 |
| 25 | 0.599 | 36.3 | 15 | 3 | 5 | 5.5 |
| 26 | 0.607 | 35.1 | 15 | 3 | 5 | 6 |
| 27 | 0.661 | 27.1 | 15 | 3 | 5 | 6.5 |
| 28 | 0.58 | 39.1 | 15 | 3 | 10 | 6.5 |
| 29 | 0.489 | 52.7 | 15 | 3 | 10 | 7.5 |
| 30 | 0.607 | 35.1 | 15 | 3 | 5 | 6.5 |
| 31 | 0.522 | 47.8 | 15 | 3 | 10 | 6.5 |
| 32 | 0.636 | 30.8 | 15 | 3 | 5 | 13 |
| 33 | 0.594 | 37 | 15 | 3 | 10 | 13 |

B—Results:

Like with the tests with the card-form (diskoid) magnetic vortex, only the evaluation on 0.8% agarose gel was used to demonstrate the effectiveness of the method, given the bias introduced into the OD measurements by the impurities released by the glass beads 4.

The photograph of the gel shows first of all that, regardless of the experimental conditions, a release of nucleic acids was brought about for tests performed with the lateral vortex under references 1 to 32.

The DNA band was visible as were the two RNA bands. By comparison with the mechanical vortex, the quality of preservation of the nucleic acids was identical.

These tests allow us to define the range of settings (time, number of large-sized beads 13 or small-sized beads, not depicted in FIG. 4, height of magnets 16, rotational speed) in which the lateral magnetic vortex operates satisfactorily. It is noted that tests 1 to 7, 10, 17 to 26, 29 and 30 are highly satisfactory from the point of view of the quantity and quality of the nucleic acids released by comparison with the mechanical vortex.

The optimum setting of the lateral magnetic vortex seems to lie somewhere around the following point, for 600 $\mu$l of sample:

180 µl of VIAI glass beads 4 (100 µm), five iron beads 3 (diameter 2 mm), 10 min (the longer the duration, the greater the lysis), between 2800 and 3700 rpm for the rotational speed of the magnets about the tube, two NdFeB magnets reference EN 129-2 from, for example, Binder Magnetic, about 4 mm for the closest distance between the magnet 16 and the tube 12, and the elevation of the tube 12 with respect to the bottom of the tube sheath.

This elevation defines the relative position of the magnets 16 with respect to the tube 12.

These tests demonstrate the effectiveness of the lateral magnetic vortex. The lysis duration has a direct influence on the amount of nucleic acids released up to the saturation plateau at around about 90%.

3—Tubular Format (Longitudinal) Magnetic Vortex

A—Procedure:

The lysis protocol was performed in a tube-format container 12 of the Falcon type with a U-shaped bottom (diameter×height=12×75 mm) on *S. epidermidis* bacteria cultured the day before.

The tubes 12 were filled with a volume of 600 µl of bacterial suspension and an apparent volume of 180 µl of VIAI beads, not depicted in this FIG. 5, of diameter 100 µm then sealed with a stopper. The tube 12 was fixed to the mechanical support or bracket 17 comprising an arm, by the upper part of its body, and placed asymmetrically with respect to the rotation spindle 19 of the magnet 15. The distance between the magnet 15 and the outer bottom of the tube was set at about 2 mm. The permanent magnet 15, fixed on the rotor of the mechanical system, was of the NdFeB type, reference NE 1 030 from Binder Magnetic.

Tests were performed for various parameters, such as the number of iron beads 13 (5, 10 or 15), the vortex duration (5 or 10 min) and the rotational speed (2800 rpm, 1860 rpm and 930 rpm). The holding or not-holding of the tube in order to prevent it from vibrating was also tested.

The experimental conditions tested are summarized in table 2 below. The OD of the initial suspension was 0.672.

TABLE 2

Study into the effectiveness of a tubular format magnetic vortex subjected to longitudinal magnetization

| N °               | OD (550 nm) | Iron beads | Glass beads | Duration (min) | Speed |
|-------------------|-------------|------------|-------------|----------------|-------|
| IS (Initial Suspension) | 0.672 |            |             |                |       |
| Control           | 0.398       |            |             |                |       |
| Cavesteril 10*    | 0.365       | 5 to 15    | 0           | 10             | 9     |
| Cavesteril 5*     | 0.3         | 5 to 10    | 0           | 5              | 9     |
| 9                 | 0.313       | 10         | 0           | 10             | 9     |
| 9'                | 0.278       | 10         | 0           | 10             | 9     |
| 10                | 0.245       | 15         | 0           | 10             | 9     |
| 10'               | 0.199       | 15         | 0           | 10             | 9     |
| 21                | 0.126       | 10         | 0           | 10             | 9     |
| 22                | 0.2         | 15         | 0           | 10             | 9     |
| 11                | 0.217       | 10         | 0           | 10             | 6     |
| 11'               | 0.099       | 10         | 0           | 10             | 6     |
| 12                | 0.224       | 15         | 0           | 10             | 6     |

TABLE 2-continued

Study into the effectiveness of a tubular format magnetic vortex subjected to longitudinal magnetization

| N ° | OD (550 nm) | Iron beads | Glass beads | Duration (min) | Speed |
|-----|-------------|------------|-------------|----------------|-------|
| 12' | 0.237       | 15         | 0           | 10             | 6     |
| 13  | 0.13        | 5          | 0           | 10             | 9     |
| 14  | 0.155       | 10         | 0           | 10             | 9     |
| 15  | 0.305       | 5          | 0           | 5              | 9     |
| 16  | 0.292       | 10         | 0           | 5              | 9     |
| 17  | 0.242       | 5          | 0           | 10             | 6     |
| 18  | 0.091       | 10         | 0           | 10             | 6     |
| 19  | 0.261       | 5          | 0           | 5              | 6     |
| 20  | 0.334       | 10         | 0           | 5              | 6     |
| 30  | 0.568       | 5          | 0           | 10             | 3     |
| 31  | 0.57        | 10         | 0           | 10             | 3     |
| 32  | 0.667       | 15         | 0           | 10             | 3     |
| 36  | 0.655       | 5          | 0           | 10             | 3     |
| 37  | 0.62        | 10         | 0           | 10             | 3     |
| 33  | 0.583       | 5          | 0           | 5              | 3     |
| 34  | 0.466       | 10         | 0           | 5              | 3     |
| 35  | 0.82        | 15         | 0           | 5              | 3     |
| 38  | 0.638       | 5          | 0           | 5              | 3     |
| 39  | 0.627       | 10         | 0           | 5              | 3     |
| 40  | 0.764       | 5          | 0           | 5              | 3     |
| 41  | 0.751       | 5          | 0           | 5              | 3     |

Cavesteril 10*: This is a control based on a sterile BCC buffer (that is to say containing no microorganisms) treated by a magnetic vortex so as to determine the increase in the background noise on the OD as a result of the release of the impurities. The OD should be around 0 if no dirt is present. This is an average across 3 tubes over 10 min.
Cavesteril 5*: This is a control based on a sterile BCC buffer (that is to say containing no microorganisms) treated by a magnetic vortex so as to determine the increase in the background noise on the OD as a result of the release of the impurities. The OD should be around 0 if no dirt is present. This is an average across 3 tubes over 5 min.

B—Results:

Bacterial lysis was evaluated on 0.8% agarose gel to demonstrate the effectiveness of the method given the bias introduced into the OD measurements by the impurities released by the glass beads.

A photograph of the gel showed first of all that, under most of the experimental conditions, a release of nucleic acids was brought about for the tests performed with the longitudinal vortex, referenced 9 to 41 in table 2.

The DNA band was visible as were the two RNA bands 16 and 23S. By comparison with the mechanical vortex, referenced C for control, the quality of preservation of the nucleic acids was the same. In most of the experimental instances, the intensity of the DNA/RNA bands was equal to or greater than the mechanical vortex. Provided the optimum setting can be found for the influential parameters, the effectiveness of this magnetic vortex is therefore greater than or equal to the mechanical vortex adopted as reference.

The range of adjustment (time, number of beads, height of magnets, speed of rotation) in which the lateral magnetic vortex operates satisfactorily is therefore determined. It may be noted that tests 9, 9' and 12 to 35 were highly satisfactory from the point of view of the quantity and quality of the nucleic acids released by comparison with the mechanical vortex.

The optimum setting of the longitudinal magnetic vortex is therefore around about the following point for 600 µl of sample:

180 µl of VIAI glass beads (100 µm), five to ten iron beads 13 with a diameter of 2 mm, 10 min for the duration of the lysis, between 930 and 2800 rpm for the rotational speed of the magnets, one NdFeb magnet reference NE 1 030 from Binder Magnetic, and about 2 mm for the distance between the magnetic 15 and the tube 12.

Some advantageous features should be noted: first, the longer the duration of the lysis the more effective it is and, second, the tube 12 is left free to vibrate so as to give rise to greater agitation of the iron beads 13 and glass beads.

The effectiveness of the longitudinal magnetic vortex is therefore demonstrated, even if the optimal setting has not been correctly defined. The duration of the lysis has a direct influence on the amount of nucleic acids released up to the saturation plateau at around about 90%.

REFERENCES

1. Lysis device
2. Diskoid container
3. Large-sized grinding means
4. Small-sized grinding means
5. Permanent magnet under the container 2
6. Central stud
7. Runway
8. Intermediate area
9. Partitioning means or film
10. Support for the magnet or magnets 5
11. Lysis device
12. Tubular container
13. Large-sized grinding means
14. Support for the container 12
15. Permanent magnet under the container 12
16. Permanent magnet around the container 12
17. Bracket for the container 12
18. Support for the magnet or magnets 16
19. Rotation spindle for the magnet 15
20. Motor transmitting its power via the spindle 19
21. Rotation spindle for the support 10 and the magnets 5
22. Lateral edges of the container 2
23. Means for introducing the biological sample
24. Diskoid well
F1. Rotational motion of the support 10 for the magnets 5
F2. Rotational motion of the magnet 15
F3. Rotational motion of the support 18 for the magnets 16
D. Diameter of a large-sized grinding means 3
E. Separation between the bottom of the container 12 and the magnet 15
H. Height between the intermediate area 8 and the partitioning film 9

What is claimed is:

1. A device for the lysis of at least one species of micro-organism, so as to release at least one intracellular biological component, which comprises:
    a container defining at least one enclosure for containing a biological sample in liquid medium comprising said species of micro-organism;
    at least one large-sized magnetic particle, made of at least one material which is relatively hard and substantially inert with respect to said species of micro-organism, and which has a magnetic susceptibility, contained in said enclosure;
    a multiplicity of small-sized particles, each made of at least one material which is relatively hard and substantially inert with respect to said species of micro-organism, contained in said enclosure; and
    a means external to said container and capable of generating a variable magnetic field passing through said container and enclosure, such that said variable magnetic field directly moves said magnetic particle inside said enclosure, causing said small-sized particles to move in grinding motion with respect to said species of micro-organism.

2. A device according to claim 1, wherein said magnetic particle has a large diameter relative to said small-sized magnetic particles, and each of said small-sized particles has a small diameter relative to said magnetic particle.

3. The device according to claim 1, wherein a ratio between a diameter of each of said small-sized particles and a diameter of said magnetic particle is between 1/10 and 1/100.

4. The device according to claim 1, wherein a number of magnetic particles is between 1 and 10.

5. The device according to claim 1, wherein a ratio between a diameter of each of the small-sized particles and a diameter of the magnetic particle is between 1/30 and 1/40.

6. The device according to claim 1, wherein a number of magnetic particles is between 1 and 4.

7. The device according to claim 1, wherein the enclosure is of tubular shape.

8. The device according to claim 1, wherein the enclosure is of discoid shape.

9. The device according to claim 7, wherein the magnetic means comprises at least one rotatable permanent magnet.

10. The device according to claim 9, wherein said rotatable permanent magnet is placed under said container.

11. The device according to claim 9, wherein said permanent magnet is rotatable around said container.

12. The device according to claim 1, wherein the variable magnetic field generated by said magnetic means is alternately strong and weak.

13. The device according to claim 1, wherein a ratio between a diameter of each of the particles and a diameter of said magnetic bead is between 1/30 and 1/60.

14. The device according to claim 8, wherein said enclosure further comprises a roughly circular runway located at the periphery of the container, wherein said at least one magnetic particle and said multiplicity of small-sized particles are contained.

15. A method for the lysis of at least one species of micro-organism, so as to release at least one intracellular biological component, which comprises:
    filing an enclosure with a biological sample in liquid medium comprising said species of micro-organism;
    placing within said enclosure, with said liquid sample, at least one large-sized magnetic particle, made of at least one material which is relatively hard and substantially inert with respect to said species of microorganism, having magnetic susceptibility;
    placing within said enclosure, with said liquid sample, a multiplicity of small-sized particles, each made of at least one material which is relatively hard and substantially inert with respect to said species of micro-organism;
    fixing the position of said enclosure;
    generating a variable magnetic field passing through said enclosure, such that said variable magnetic field directly moves said magnetic particle inside said enclosure, causing said small-sized particles to move in grinding motion with respect to said species of micro-organism.

16. A method according to claim 15, wherein a ratio between a diameter of the micro-organism to be lysed and a diameter of each of the small-sized particles is between 1/10 and 1/100.

17. A method according to claim 15, wherein a ratio between a total volume of the small-sized particles and a volume of the liquid sample containing the micro-organism to be lysed is between 1/2 and 1/5.

18. A method according to claim 15, wherein a ratio between a diameter of the micro-organism to be lysed and a diameter of each of the small-sized particles is between 1/30 and 1/60.

19. A method according to claim 15, wherein a ratio between a diameter of the micro-organism to be lysed and a diameter of each of the small-sized particles is between 1/30 and 1/50.

20. A method according to claim 15, wherein a ratio between a total volume of the small-sized particles and a volume of the liquid sample containing the micro-organism to be lysed is 1/3.

21. A method according to claim 15, wherein said biological sample in liquid medium is put in vortex-type motion by the movement of said at least one magnetic particle with said small-sized particles.

22. A method according to claim 21, wherein said vortex-type motion is lateral.

23. A method according to claim 21, wherein said vortex-type motion is longitudinal.

* * * * *